US00PP26110P3

(12) United States Plant Patent
Korlipara

(10) Patent No.: US PP26,110 P3
(45) Date of Patent: Nov. 17, 2015

(54) ***ECHINACEA* PLANT NAMED 'DIXIE SCARLET'**

(50) Latin Name: ***Echinacea* spp.**
Varietal Denomination: Dixie Scarlet

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 184 days.

(21) Appl. No.: 13/998,610

(22) Filed: Nov. 14, 2013

(65) Prior Publication Data

US 2015/0135386 P1 May 14, 2015

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

Terra Nova Nurseries—Mobile—Introduction—E, retrieved on Jul. 7, 2015, retrieved from the Internet at <http://www.terranovanurseries.com/mobile/pages/introductions_e.html> 3 pp.*

* cited by examiner

*Primary Examiner* — June Hwu
(74) *Attorney, Agent, or Firm* — Klarquist Sparkman, LLP

(57) ABSTRACT

A new and distinct *Echinacea* plant named 'Dixie Scarlet' characterized by an amazing number of inflorescences starting in the first season, very long bloom time with excellent rebloom, a very upright, compact habit, bright scarlet ray florets surrounding dark cones, numerous, strong dark stems, and excellent vigor.

1 Drawing Sheet

Botanical denomination: *Echinacea* spp.
Variety designation: 'Dixie Scarlet'.

BACKGROUND OF THE INVENTION

The present invention relates to a new and distinct cultivar of *Echinacea* and given the cultivar name 'Dixie Scarlet'. *Echinacea* is in the family Asteraceae. The new cultivar is part of a planned breeding program for a landscape series with compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Tomato Soup' (U.S. Plant Pat. No. 19,427), the new cultivar has a smaller, narrower, more compact habit, smaller flowers, and narrower leaves.

Compared to *Echinacea* 'Firebird' (U.S. Plant Pat. No. 22,775), the new cultivar has a flatter inflorescence.

Compared to *Echinacea* 'Balsomsed' (U.S. Plant Pat. No. 23,105), the new cultivar has longer ray florets, a flatter inflorescence, a narrower habit and a brighter, more orange red than red flower color.

This new *Echinacea* cultivar is uniquely distinguished by:

1. an amazing number of inflorescences starting in the first season,
2. very long bloom time with excellent rebloom,
3. very upright, compact habit,
4. bright scarlet ray florets surrounding dark cones,
5. numerous, strong dark stems, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the inflorescences of *Echinacea* 'Dixie Scarlet' as a two-year-old growing in the trial field in full sun in mid-July in Canby, Oreg.

FIG. 2 shows the inflorescences and habit of the same plant.

DETAILED PLANT DESCRIPTION

The following is a detailed description of the new *Echinacea* cultivar based on observations of 18-month-old specimens growing in the garden in sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition.

Plant:

*Type.*—Herbaceous perennial.
*Hardiness.*—USDA Zones 4 to 9.

*Size.*—Grows to about 31 cm wide and 45 cm tall to top of inflorescences.

*Form.*—Basal clump, with about 10 stems from the base.

*Vigor.*—Excellent.

*Roots.*—Fibrous, with many downward growing and few laterals, ivory in color, Yellow White 158D, roots develop easily from cuttings from the crown.

Leaf (stem):

*Type.*—Simple.

*Shape.*—Lanceolate.

*Arrangement.*—Alternate.

*Blade size.*—Grows to 7.5 cm long and 1.5 cm wide.

*Margins.*—Shallowly, unevenly senate.

*Apex.*—Acuminate.

*Base.*—Attenuate.

*Surface texture.*—Strigose on both sides.

*Venation.*—Pinnate, Yellow Green 147D on both sides.

*Color.*—Topside Green N137A, bottom side closest to Yellow Green 147A.

*Petiole description.*—Clasping, grows to 4 cm long and 3 mm wide, scabrous, narrow leafy edges which fold upwards, topside Green N137A, bottom side closest to Yellow Green 147A.

Inflorescence:

*Type.*—Composite on terminal stalked heads.

*Number of flowering stems from the ground.*—About 10.

*Flowering stem.*—Grows to 38 cm tall from the base of the plant to the terminal inflorescence and can grow to 16.5 cm long from the top stem leaf to the base of an inflorescence; unbranched to branched, with 1 to 4 inflorescences per stem; diameter growing to 7 mm wide near the inflorescence; strigose; Yellow Green 147B in shade and heavily stippled 187A in sun.

*Size.*—Grows to 9.5 cm wide and 4 cm deep as disc enlarges.

*Form.*—Ray florets held horizontally, mature disc is conic.

*Immature inflorescence.*—4 cm wide and 2.8 cm deep, ray florets held upright at an 85 degrees and rolled up so only the back color shows, Greyed Purple N186D except tip Green Yellow 1C, disc color Yellow Green 144A in center ½ to Greyed Orange 176B outside ½.

*Ray florets.*—Without pistil or stamen, 15 to 20 in number, grow to 49 mm long and 13 mm wide, oblanceolate with the tip two-toothed (each acute), entire margins, base attenuate, glabrous on both sides; topside Red 45A; bottom side Greyed Red 181A.

*Disc.*—Flat becoming conic, becoming 20 mm deep and 29 mm wide with maturity, Greyed Purple 187A in background with bracts Orange 16C with tips Greyed Purple 187A.

*Disc florets.*—About 150 in number, each with 1 pistil and 4 stamen, grow to 11 mm long and 2.5 mm wide, each with one persistent, very stiff linear bract (14 mm long with the top 4.5 mm Greyed Purple 187A to 4 mm Yellow Green 146B blending to White NN155A on bottom); corolla 6 mm long and 2 mm wide, tubular, 5 lobed, glabrous, Greyed Purple 183A; pistil 11 mm long, ovary 3.5 mm long, White NN155D with top Yellow Green 144A, style 6 mm long White NN155A, 2-branched stigma spreading 2.5 mm wide, Greyed Purple 187A; stamen 4.5 mm long, filaments 2 mm long and White NN155B, anthers 2 mm long and Greyed Brown N199A, pollen none.

*Involucral bracts.*—In 4 leafy series, area grows to 30 mm wide and 10 mm deep, lobes lanceolate in shape, reflexed, grow to 10 mm long and 2 mm wide, Green N137A, margins strigose, tip acute, strigose on both sides.

*Receptacle.*—Grows to 8 mm wide and 10 mm deep, White NN155B.

*Bloom period.*—June through October in Canby, Oreg.

*Fragrance.*—Floral, sweet.

*Lastingness.*—Each inflorescence lasts about two weeks in Canby, Oreg.

Seeds: 3 mm long and 2.5 mm wide, oval, Brown 200C.

*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

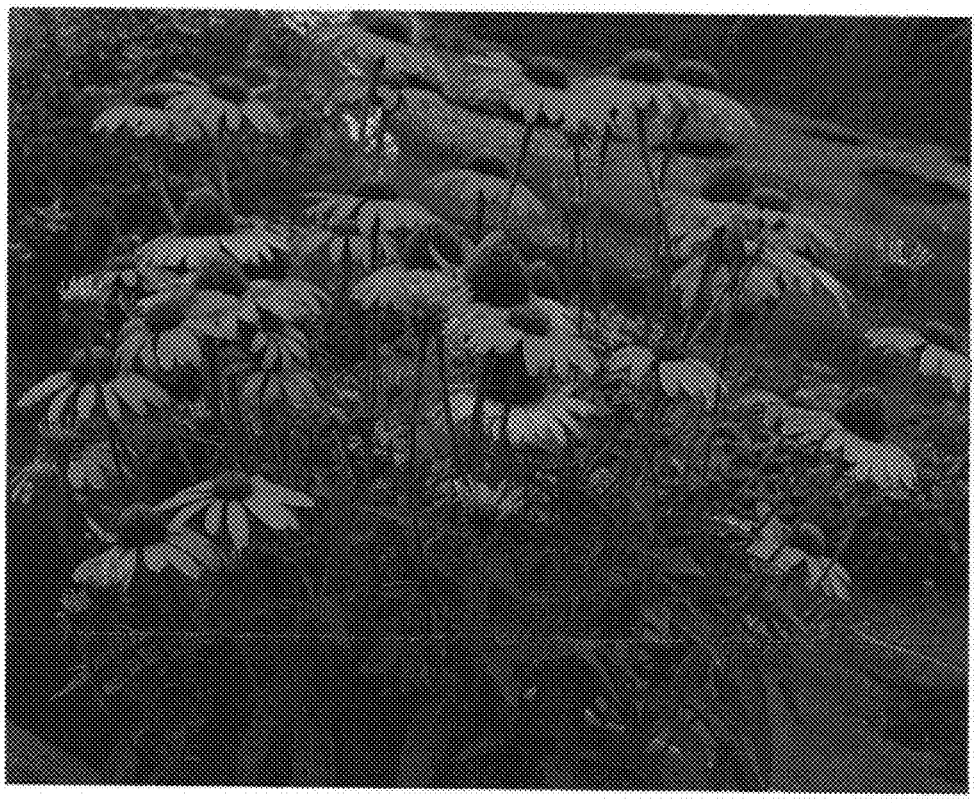

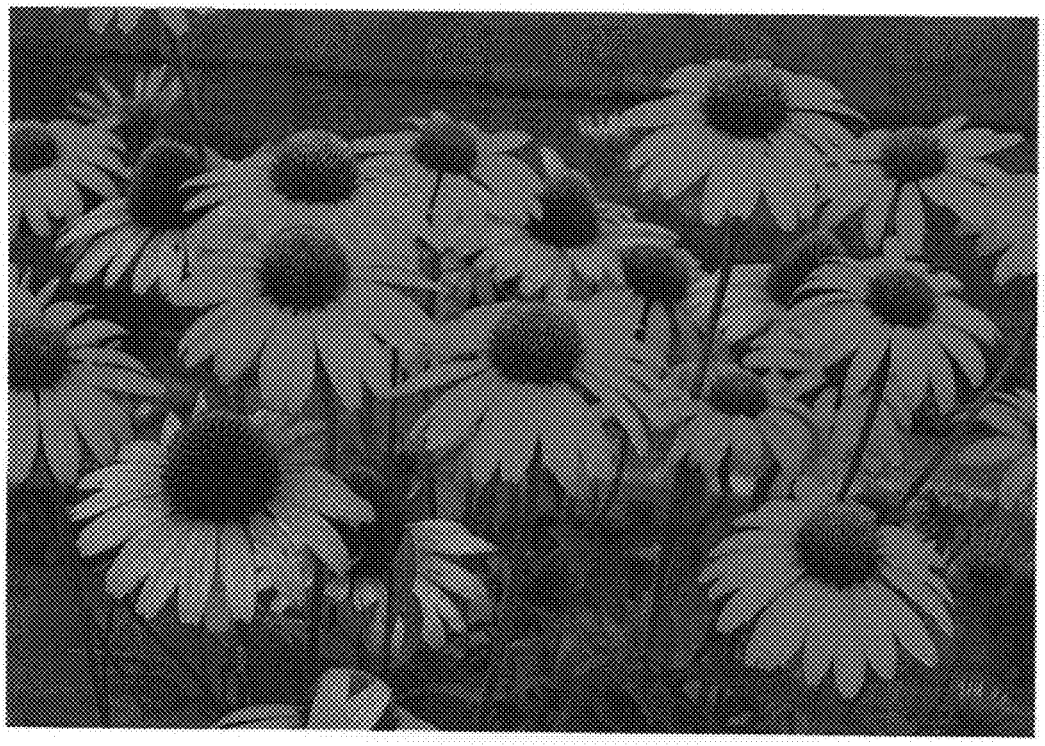
FIG. 1 above, FIG. 2 below